United States Patent [19]

Wehrenberg

[11] Patent Number: 4,540,804

[45] Date of Patent: Sep. 10, 1985

[54] HERBICIDE INTERMEDIATES

[75] Inventor: Peter K. Wehrenberg, El Cerrito, Calif.

[73] Assignee: Stauffer Chemical Company, Westport, Conn.

[21] Appl. No.: 660,171

[22] Filed: Oct. 12, 1984

[51] Int. Cl.³ .............................................. C07C 69/76
[52] U.S. Cl. ............................... 560/060; 260/544 D; 549/274
[58] Field of Search .......................................... 560/60

[56] References Cited

FOREIGN PATENT DOCUMENTS 95148 8/1981 Japan ..................................... 560/60

OTHER PUBLICATIONS

Heathcock, C. H., J. Org. Chem., 45(19), 3846–56, (1980).

*Primary Examiner*—Paul J. Killos
*Attorney, Agent, or Firm*—Paul R. Martin

[57] ABSTRACT

An alkyl 3-hydroxy-4-(4-hydroxyphenoxy)pentanoate having the formula

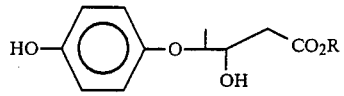

wherein R is an alkyl or substituted alkyl group ranging from about 1 to about 18 carbon atoms.

9 Claims, No Drawings

HERBICIDE INTERMEDIATES

BACKGROUND OF THE INVENTION

The present invention relates to alkyl 3-hydroxy-4-(4-hydroxyphenoxy)pentanoates, compounds used as critical intermediates in the production of aryloxy phenoxy pentanoate herbicides.

Aryloxyphenoxy alkyl acids and esters are well known herbicides and have been found to be particularly useful as post-emergent herbicides when used against grassy-type weed pests. These aryloxyphenoxy herbicides can be made a number of different ways, however, the primary method described in the literature comprises initially reacting a pyridine-type compound with a hydroquinone, followed by completion of subsequent processing steps. This method is described in U.S. Pat. Nos. 4,152,328 and 4,216,007. A problem with this method is that the initial starting compound, the pyridine-type compound, is very expensive, and subsequent processing steps dilute the percentage of pyridine moiety ending up in the end product, thus increasing significantly the cost of the final product which is obtained.

Desirably, the pyridine moeity is added at the end of the process in order to maximize the percent yield, and minimize the expense of the pyridine-type compound.

The present invention is thus concerned with intermediates for the aryloxy phenoxy-type herbicides which intermediates enable the pyridyl moiety to be added at the end of the entire process. Such intermediates are alkyl 3-hydroxy-4-(4-hydroxyphenoxy)pentanoates.

DESCRIPTION OF THE INVENTION

A new compound has now been discovered which is a useful intermediate in producing a specific aryloxypentanoate herbicide.

This new compound is alkyl 3-hydroxy-4-(4-hydroxyphenoxy)pentanoate. This compound has the formula

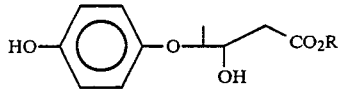

wherein R is selected from the group consisting of an optionally substituted alkyl group having from 1 to 18 carbon atoms.

The subject compound can be prepared in a series of reactions beginning with 4-benzyloxyphenol as a starting compound. In general, the method comprises the steps of (a) reacting 4-benzyloxyphenol with an alkali hydroxide and 2-chloropropionic acid in the presence of a suitable solvent and at a temperature sufficient to cause formation of 2-(4-benzyloxyphenoxy)propionic acid;

(b) reacting said 2-(4-benzyloxyphenoxy)propionic acid with phosgene, oxalyl chloride, thionyl chloride or phosphorus trichloride, in the presence of a suitable catalyst and solvent and at a temperature sufficient to cause formation of 2-(4-benzyloxyphenoxy)propionyl chloride;

(c) reacting said 2-(4-benzyloxyphenoxy)pripionyl chloride with 2,2-dimethyl-1,3-dioxan-4,6-dione and pyridine, all in the presence of a suitable solvent and at a temperature sufficient to cause formation of 5-[2-(4-benzyloxyphenoxy)propionyl]-2,2-dimethyl-1,3-dioxan-4,6-dione;

(d) reacting said 5-[2-(4-benzyloxyphenoxy)propionyl]-2,2-dimethyl-1,3-dioxan-4,6-dione with an optionally substituted alkyl alcohol for a period of time and at a temperature sufficient to cause formation of alkyl 4-(4-benzyloxyphenoxy)-3-oxopentanoate;

(e) reacting said alkyl 4-(4-benzyloxyphenoxy)-3-oxopentanoate with sodium borohydride in the presence of a suitable solvent and at a temperature sufficient to cause formation of alkyl 4-(4-benzyloxyphenoxy)3-hydroxypentanoate; and (f) reacting said alkyl 4-(4-benzyloxyphenoxy)-3-hydroxypentanoate with hydrogen in the presence of a suitable solvent, a suitable catalyst, and at a sufficient temperature to form the desired product, alkyl 3-hydroxy-4-(4-hydroxyphenoxy)pentanoate.

Alternatively, steps (e) and (f) may be reversed and step (e) may be replaced by a catalytic hydrogenation, possibly in combination with step (f).

This process can be represented schematically as set forth below, a preferred process being indicated.

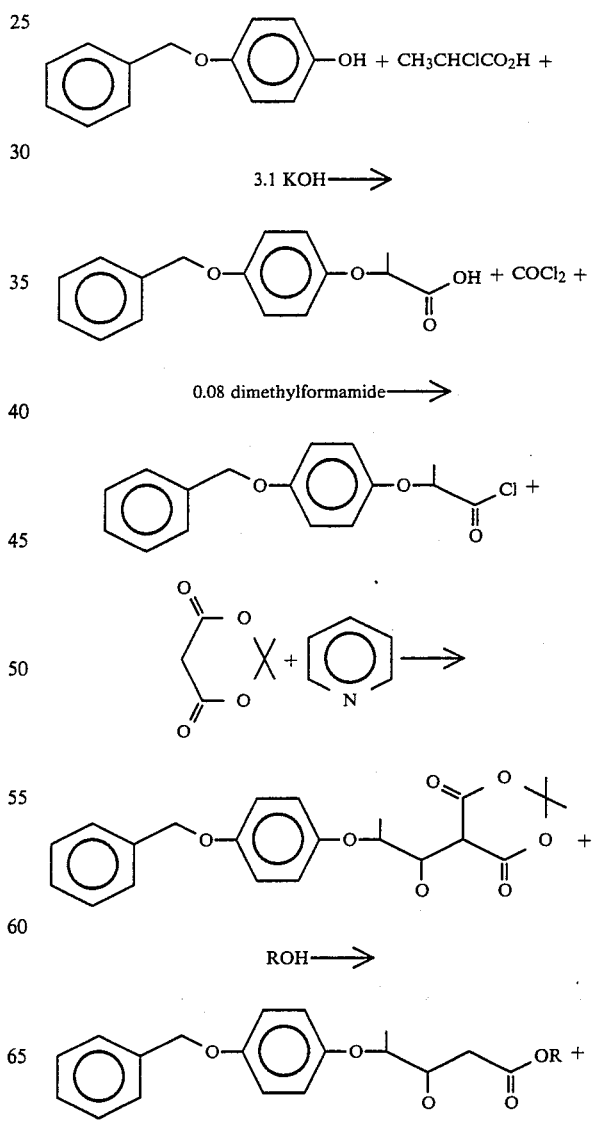

-continued

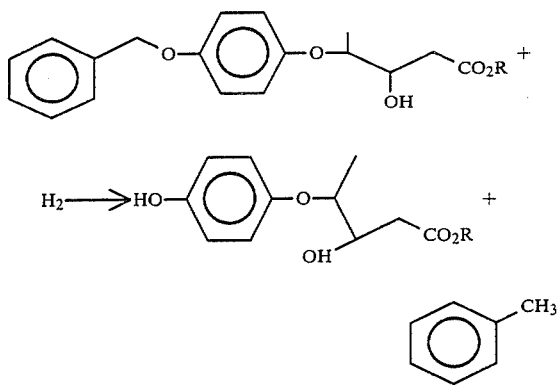

wherein R is an alkyl or substituted alkyl group having from about 1 to 18 carbon atoms.

Potassium hydroxide is the preferred alkali hydroxide for use in step (a) of the invention; however, sodium hydroxide would also be suitable. In addition, toluene is the preferred solvent, but other organic solvents of the same or similar type would be acceptable.

The temperature of the first step of the reaction in accordance with the preferred embodiment is normally carried out between about 20° to about 150° C., with 85° C. being preferred.

In step (b) of the reaction of the invention, the preferred compound for reacting with 2-(4-benzyloxyphenoxy)propionic acid is phosgene. However, other phosgene substitutes can be used, such as oxalyl chloride, thionyl chloride or phosphorus trichloride. In addition, the preferred catalyst is dimethylformamide, but other catalysts, such as imidazole, tertiary amines and amides could be used. Again, toluene is the preferred solvent and the reaction is normally carried out between about 0° C. and 140° C., with 70° being preferred.

In step (c) of the process of the invention, methylene dichloride is preferred for use as the solvent. Other suitable solvents would include hydrocarbons and halocarbons such as toluene and chloroform.

The reaction is conventionally carried out at between −40° C. and 80° C. 2,2-Dimethyl-1,3-dioxan-4,6-dione, one of the reactants in step (c) of the process, is commonly known as Meldrum's acid.

In step (d) of the process of the invention, ethyl alcohol is the preferred reactant to combine with the Meldrum's acid adduct, 5-[2-(4-benzyloxyphenoxy)propionyl]-2,2-dimethyl-1,3-dioxan-4,6-dione; however other alkanols such as methanol, isopropanol, etc. could be used. When ethanol is the alcohol of choice, the reaction is normally carried out at a temperature range between about 20° C. and about 150° C., with 60° C. being preferred.

Any alcohol having a carbon chain ranging from about 1 to about 20 carbon atoms can be used.

In step (e) of the process the reaction is normally carried out in the presence of ethyl alcohol; however other solvents such as methanol, isopropanol, etc., corresponding to the alkanol of step (d) could be used. The reaction is normally carried out at temperatures ranging from −40° to about 80° C.

In the next step of the reaction (step f), the hydrogenation step, the preferred catalyst is a palladium/carbon catalyst and the reaction is carried out in the same solvent as step (e) and hydrochloric acid at a temperature ranging from about 0° to about 150° C.

This invention will be more clearly understood by reference to the following examples, which are intended to be illustrative of the process, but not limiting thereof.

EXAMPLE I

Preparation of Benzyloxyphenoxypropionic Acid

A three-liter, four-necked, round-bottom flask was obtained and fitted with a thermocouple and temperature controller, a heating mantle, and addition funnel, a nitrogen line connected to a nitrogen/vacuum source, a condenser, an overhead stirrer, and a catch basin. Into this flask was charged 420 grams (g) (2.1 moles) of benzyloxyphenol, 216.2 g (5.4 moles) sodium hydroxide, and 700 milliliters (ml) toluene. Additionally, 250 ml (2.9 moles) of chloropropionic acid was charged into the funnel and nitrogen was added to replace the atmosphere in the flask. The contents were then heated to 95° C. with stirring. The reaction was conducted over a period of several hours, and during that time quantities of chloropropionic acid were added to prevent solidification of the reaction materials. During the same period of time an additional quantity of sodium hydroxide was added to facilitate the reaction.

At the end of the first day, the stirring was stopped, and the flask left under a nitrogen atmosphere overnight. The next day, the flask was heated to 95° C. and more chloropropionic acid (60 ml) was added. After about 4 additional hours of addition of chloropropionic acid the reaction was stopped and the subject propionic acid product was isolated.

EXAMPLE II

Preparation of Benzyloxyphenoxypropionyl Chloride

A three-liter, round-bottom flask was obtained and fitted with an overhead stirrer, a thermocouple, a temperature controller, an addition funnel with a cold trap overhead, and a line leading to a phosgene cylinder. Also it was fitted with an exit line to a nitrogen/vacuum source, a heating mantle, and a catch basin. The exit line went to a condenser and a caustic scrubber. Into this flask was placed 183.2 g (0.67 mole) benzyloxyphenoxypropionic acid, 900 ml of toluene, and 2.9 g (0.04 mole) dimethylformamide. The phosgene cyclinder was turned on and 75 ml (1.05 moles) phosgene was allowed to accumulate in the funnel. The reactants were heated to 80° C. with stirring while the phosgene was added thereto. During the course of the phosgene addition, solids formed in the flask; however, ultimately they went into solution. After the phosgene addition, nitrogen was slowly added to the flask. The reaction was stopped, and a vacuum pulled on the flask to boil off the excess phosgene. The flask was then placed under a nitrogen atmosphere. The solvent was stripped off, leaving 233.2 g of yellow solids, which were identified by suitable analytical techniques as being the subject compound.

EXAMPLE III

Preparation of
5-[2-(4-Benzyloxyphenoxy)pripionyl]-2,2-dimethyl-1,3-dioxan-4,6-dione A three-liter, four-neck flask equipped with a thermometer, overhead stirrer, addition funnel, and a line to a nitrogen/vacuum source was obtained and placed in a dry ice/isopropanol bath. To the flask was charged 281.0 ml (1.95 moles) of Meldrum's acid, 600 ml of methylene dichloride, and 290 ml (3.6 moles) pyridine. The contents were then cooled to −10° C. and placed under the nitrogen atmosphere. Benzyloxyphenoxypropionyl chloride (596.5 g, 1.71 mole) was dissolved in 300 ml methylene dichloride, and placed in an addition funnel. The contents of the addition funnel were then added to the round-bottom flask over a period of time. Approximately two hours after the addition was complete, 307 ml concentrated hydrochloric acid in ice and enough ice water to fill the flask were added. The contents were then poured into a separation funnel, the flask rinsed, and 100 ml of a 1:1 methylene dichloride-:ice water aqueous solution was added to the funnel. The material then solidified, and to this was added one liter methylene dichloride which caused a separation of the contents into an organic phase and an aqueous phase. The organic phase contained a quantity of solids. The aqueous phase was removed and the organic phase and solids were stirred with 600 ml ice water and enough methylene dichloride to dissolve the solids (approximately 600 ml). The phases were then separated, and the organic phase dried over sodium sulfate, and stripped on a rotary evaporator. When the organic phase was mostly stripped, but still containing a considerale amount of solvent, 600 ml anhydrous ethanol was added to prevent the product from crystallizing in an unworkable form and the reaction vessel placed in a refrigerator. The contents were later analyzed by suitable analytical techniques and found to be the subject compound dissolved in solvent.

EXAMPLE IV

Synthesis of Ethyl
4-(4-benzyloxyphenoxy)-3-oxopentanoate

A three-liter, four-necked, round-bottom flask equipped with a heating mantle, a catch basin, a condenser, thermometer, overhead stirrer, and a line to a nitrogen/vacuum source was obtained, and into this flask was placed 681 g (1.71 mole) of the Meldrum's acid adduct prepared in accordance with Example III above, along with a quantity of ethanol, and the reactants were then heated and stirred under a nitrogen atmosphere. As the contents were heated, some refluxing and off-gassing occurred, and most of the solids dissolved, with concomitant off-gassing. After approximately 3 hours, the heating was stopped and the stirring stopped. The reaction mixture was then stripped on a rotary evaporator at 50° C., and there was obtained 605.7 g of an oil, identified by analytical techniques as being the subject compound.

EXAMPLE V

Synthesis of Ethyl
4-(4-benzyloxyphenoxy)-3-hydroxypentanoate

A three-liter, four-necked flask fitted with an overhead stirrer, thermometer, a line to a nitrogen/vacuum source via a Firestone valve, and a water/ice bath underneath was obtained. To this flask was charged 580.1 g (1.70 mole) of the beta-ketoester formed in accordance with Example IV above, 1000 ml of ethanol, and 22.1 g (0.58 mole) of sodium borohydride, which was added portion wise over a period of time, checking the extent of the reaction after each addition. Thereafter 800 ml each of water and methylene dichloride were added, and the phases separated. The organic phase was washed with 600 ml of water and 150 ml saturated ammonium chloride solution. The phases were again separated. The organic phase was dried over sodium sulfate, stripped with a rotary evaporator at approximately 50° C. There was obtained 520.5 g of an oil. The HPLC showed the product to be the subject compound.

EXAMPLE VI

Synthesis of Ethyl
3-hydroxy-(4-hydroxyphenoxy)pentanoate

A three-liter, four-neck flask with a round bottom, equipped with a mechanical stirring device, a thermometer, a gas inlet, and a Firestone valve, was obtained and into this flask was charged 499.5 g (1.46 mole) of the beta-keto ester compound formed in accordance with Example V above, and 1600 ml of ethanol and then placed under a nitrogen atmosphere. Eleven grams of a palladium or carbon catalyst was then added and the atmosphere exchanged several times for nitrogen. The Firestone valve was then closed and the line removed from the nitrogen and placed on a hydrogen cylinder and the hydrogen flow was adjusted with the Firestone valve closed. The flask was evacuated and the atmosphere exchanged two times with hydrogen and the hydrogen flow was then adjusted to the slowest bubbling rate from the Firestone valve. After several hours had elapsed, the mixture was filtered and stripped with a rotary evaporator and there was obtained 408.9 g of a dark oil which was identified as being the subject compounds, namely, ethyl 3-hydroxy-4-(4-hydroxyphenoxy)pentanoate.

The alkyl 3-hydroxy-4-(4-hydroxyphenoxy)pentanoates, the novel compounds of this invention, can then be used to produce herbicidally effective aryloxy phenoxy pentanoates by reacting the intermediate with various substituted pyridine compounds, as illustrated in the following general type reaction schematically indicated below.

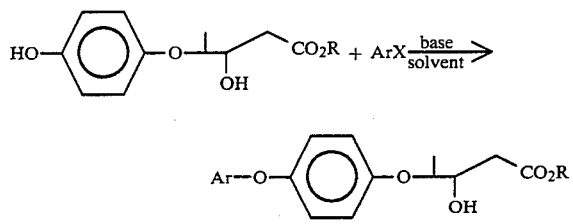

where A is a substituted phenyl or pyridyl group.

It will be recognized by those skilled in the art that variations in molar ratios, times, temperatures, and solvents used in the various steps in the process of the invention can be made without departing from the spriit and scope of the claims as appended.

What is claimed is:

1. An alkyl 3-hydroxy-4-(4-hydroxyphenoxy)pentanoate having the formula

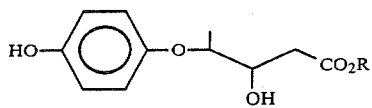

wherein R is an optionally substituted alkyl group ranging from about 1 to about 18 carbon atoms.

2. The compound of claim 1 wherein R is ethyl.

3. The compound of claim 1 wherein R is methyl.

4. A method for the preparation of alkyl 3-hydroxy-4-(4-hydroxyphenoxy)pentanoate which comprises reacting a compound of the formula

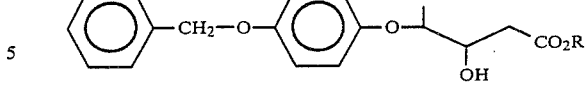

where R is an optionally substituted alcohol $C_1$–$C_{18}$; with hydrogen in the presence of a palladium/carbon catalyst and an ethanol solvent.

5. The method of claim 4 wherein R is ethyl.

6. The method of claim 4 wherein R is methyl.

7. The method of claim 4 wherein the temperature of reaction ranges from about 20° to 150° C.

8. The method of claim 4 wherein the catalyst consists of a palladium/carbon catalyst.

9. The method of claim 8 wherein the solvent used is selected from ethanol, methanol, acetone, ethylacetate, optionally mixed with water.

* * * * *